US00PP14116P39

(12) United States Plant Patent
Osiecki

(10) Patent No.: US PP14,116 P3
(45) Date of Patent: Aug. 26, 2003

(54) PHILODENDRON PLANT NAMED 'ROJO CONGO'

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 28 days.

(21) Appl. No.: 10/012,086

(22) Filed: Dec. 11, 2001

(65) Prior Publication Data

US 2003/0110547 P1 Jun. 12, 2003

(51) Int. Cl.[7] ..... A01H 5/00

(52) U.S. Cl. ..... Plt./381

(58) Field of Search ..... Plt./381

*Primary Examiner*—Bruce R. Campell
*Assistant Examiner*—Susan B. McCormick

(57) ABSTRACT

A new and distinct cultivar of Philodendron is provided. It is a large plant; suitable for production in 15-cm and larger containers; self-heading, not vining, and self-supporting; mostly upright, somewhat outwardly spreading and open; with very vigorous growth; large, thick, very dark green leaf blades; and thick, dark purple-brown petioles.

2 Drawing Sheets

Botanical classification/cultivar designation: Philodendron hybrid-cultivar 'Rojo Congo'.

BACKGROUND OF THE INVENTION

This invention relates to a new and distinct cultivar of philodendron plant, botanically known as Philodendron hybrid, and hereinafter referred to by the cultivar name 'Rojo Congo'.

The new cultivar is a product of a planned breeding program conducted by the Inventor in Altha, Fla. The objective of the program was to develop new vigorous, self-heading, not vining and self-supporting Philodendron cultivars useful for various container sizes, with attractive plant form and colors, with large, thick leaves and petioles shorter than the male parent.

The new Philodendron was discovered and selected by the Inventor in 1996 as a seedling within the progeny of a cross made in 1995 in a controlled environment in Altha, Fla. The female parent was Philodendron cultivar 'Imperial Red', disclosed in U.S. Plant Pat. No. 6,337 (species not named in the disclosure). The male parent was an unidentified selection of the *Philodendron tatei* Krause spp. *melanochlorum* (Bunting) Bunting (not patented).

Asexual propagation of 'Rojo Congo' since 1998 by means of tissue culture in Altha, Fla. has established that the unique characteristics of this new cultivar are in fact stable and reproduced true to type in successive generations.

BRIEF SUMMARY OF THE INVENTION

The new Philodendron cultivar has not been observed under all possible environmental conditions. The phenotype may vary somewhat with variations in environment and/or horticultural practices such as temperature, light intensity, day length, fertilization, irrigation, propagation procedures etc., without any variance in genotype.

The following traits have been repeatedly observed and in combination distinguish 'Rojo Congo' as a new and distinct cultivar of Philodendron:

1. Large size plant, appropriate for 15-cm and larger containers;
2. self-heading, not vining, self-supporting, mostly upright, somewhat outwardly spreading and open growth habit;
3. very vigorous growth;
4. large, thick, leathery, dark green mature leaf blades;
5. thick, very dark purple-brown mature petioles;
6. brown-maroon-green young leaves;
7. long, red-purple, relatively long-lasting petiole sheaths;
8. numerous aerial roots with distinct red zone.

Plants of 'Rojo Congo' are distinguished from plants of the female parent, commercial Philodendron cultivar 'Imperial Red' disclosed in U.S. Plant Pat. No. 6,337 by the following characteristics:

1. Plants of 'Rojo Congo' are larger, have more outwardly spreading and open growth habit than plants of 'Imperial Red'.
2. Plants of 'Rojo Congo' are more vigorous than plants of 'Imperial Red'.
3. Leaf blades of 'Rojo Congo' are thicker, larger and more ovate than leaf blades of 'Imperial Red'.
4. Petioles of 'Rojo Congo' are longer and thicker than petioles of 'Imperial Red'.
5. Mature leaf blades of 'Rojo Congo' are darker green with greater contrast between midrib and surrounding tissue than mature leaf blades of 'Imperial Red'.
6. Mature petioles of 'Rojo Congo' are dark purple-brown, whereas mature petioles of 'Imperial Red' are brownish-green.
7. Leaf petiole sheaths of 'Rojo Congo' are longer and darker red-purple than leaf petiole sheaths of 'Imperial Red'.
8. Plants of 'Rojo Congo' have more and thicker air roots than plants of 'Imperial Red'.

Plants of 'Rojo Congo' are distinguished from plants of the male parent, unidentified selection of the *Philodendron*

*tatei* spp. *melanochlorum* by its smaller size; more compact and fuller growth habit; much more vigorous growth; smaller and darker green leaf blades; shorter, dark purple-brown petioles (as opposed to green petioles of the parent plant); and longer-lasting, red-purple petiole sheaths (as oppose to yellow-green petiole sheath of the parent plant).

The new cultivar can be compared to the commercial Philodendron cultivar 'Congo' is disclosed in U.S. Plant Pat. No. 11,724.

Plants of the new Philodendron cultivar differ from plants of Philodendron 'Congo' in the following characteristics:

1. Plants of 'Rojo Congo' are narrower, have more upright, less spreading and slightly less open growth habit than plants of 'Congo'.
2. Plants of 'Rojo Congo' are more vigorous than plants of 'Congo'.
3. Leaf blades of 'Rojo Congo' are shorter, with lower length to width ratio, shorter tip, more asymmetric base than leaf blades of 'Congo'.
4. Mature leaf blades of 'Rojo Congo' are darker green with less contrasting midrib than leaf blades of 'Congo' and have red-purple margin, whereas leaf blades of 'Congo' and have light green margin.
5. Petioles of 'Rojo Congo' are shorter than petioles of 'Congo'.
6. Mature petioles of 'Rojo Congo' are dark purple-brown, whereas mature petioles of 'Congo' are green.
7. Unfolding leaves of 'Rojo Congo' have brown-maroon coloration on the blades and red-purple coloration on petioles, whereas unfolding leaves of 'Congo' are completely green.
8. Petiole sheaths of 'Rojo Congo' are longer-lasting and are red-purple, whereas petiole sheaths of 'Congo' are predominantly yellow-green.
9. Sheaths covering inflorescences of 'Rojo Congo' are red-purple, whereas sheaths covering inflorescences of 'Congo' are predominantly yellow-green.
10. Plants of 'Rojo Congo' have more aerial roots than plants of 'Congo'.

BRIEF DESCRIPTION OF THE PHOTOGRAPHS

The accompanying photographs illustrate the appearance of the new Philodendron cultivar, showing the colors as true as it is reasonably possible in color reproductions of this type. Colors in the photographs may appear slightly different from the color values cited in the botanical description, which accurately describe the actual colors of the plants of the new cultivar. The plant of 'Rojo Congo' depicted in the photographs was approximately 16 months from planting a single tissue culture-produced microcutting, and was grown in a 25-cm container.

In the photographs:

DETAILED BOTANICAL DESCRIPTION

Figure 1:
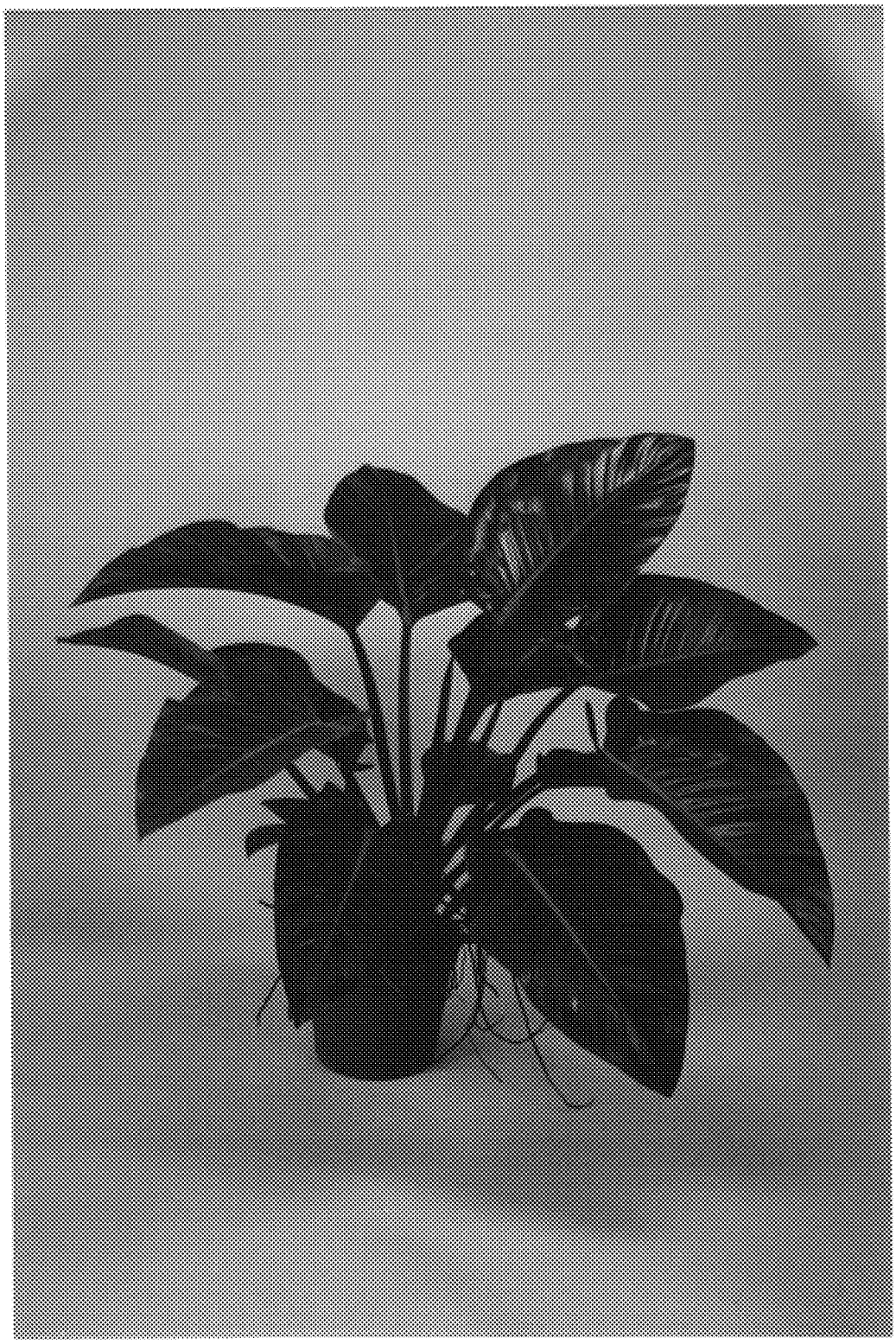
FIG. 1 depicts the whole plant.
Figure 2:
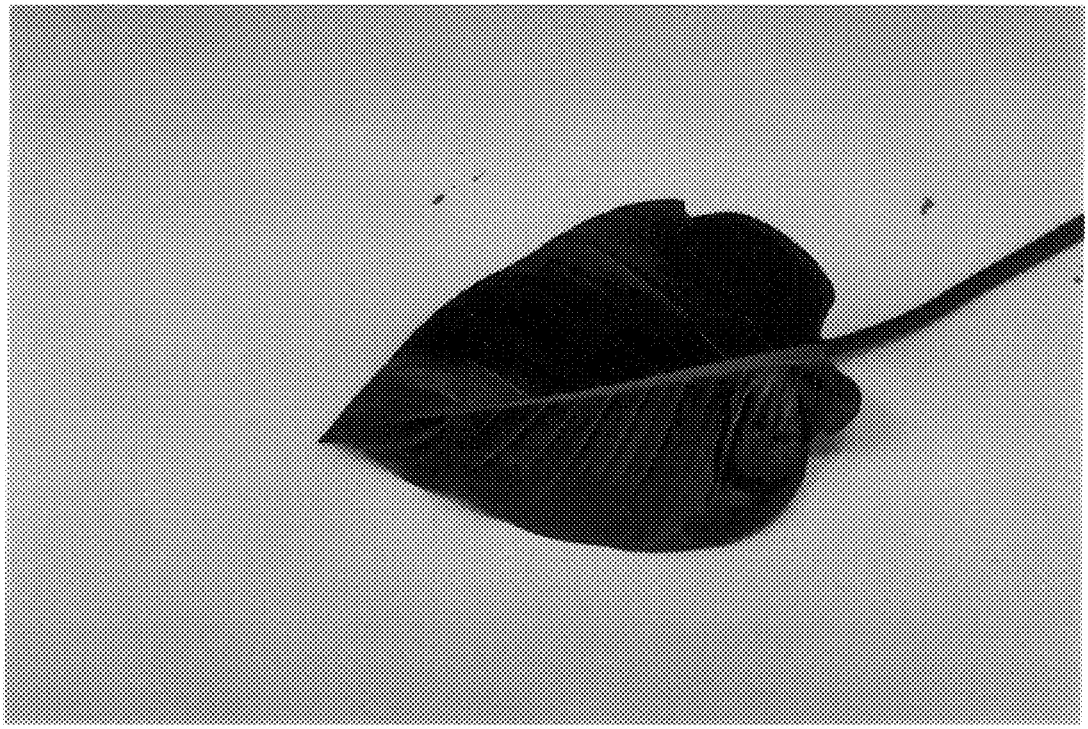
FIG. 2 illustrates the adaxial side of a mature leaf.
Figure 3:
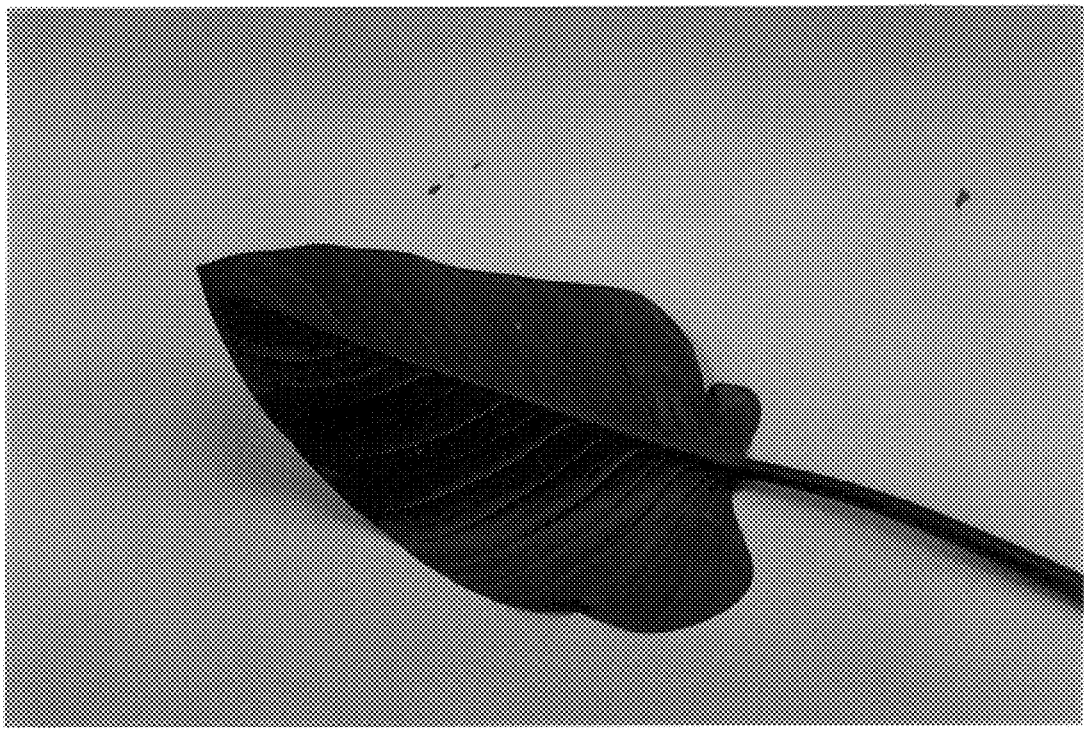
FIG. 3 illustrates the abaxial side of a mature leaf.

The following observations and measurements were recorded in September 2001 on plants grown in a polycarbonate-covered greenhouse in Altha, Fla. under conditions which closely approximate those used in commercial horticultural practice. During growth of these plants day temperature in the greenhouse ranged between 23° C. and 28° C., night temperature ranged between 21 C. and 23° C., and light level ranged between 800 and 1500 foot-candles. Plants used for these observations were grown as single plants in 25-cm containers and were about 16 months from planting tissue culture-produced microcuttings.

Mature, fully developed plant organs were used for the following observations and measurements unless otherwise indicated. Second fully unfolded leaf from the top was used for mature leaf description. Free petiole sheath at the base of the unfolding or newly unfolded leaf was used for petiole sheath description. Numerical measurements represent means from typical plants of 'Rojo Congo'. Color references are made to The R.H.S. Color Chart, except where general color terms of ordinary significance are used. Color values were determined under natural light of approximately 1200 to 1800 foot-candles.

Botanical classification: Philodendron hybrid cultivar 'Rojo Congo'.

Parentage:

*Female parent.*—Philodendron cultivar 'Imperial Red', disclosed in U.S. Plant Pat. No. 6337 (species not named in the disclosure).

*Male parent.*—Unidentified selection of the *Philodendron tatei* Krause spp. *melanochlorum* (Bunting) Bunting (not patented).

Propagation:

*Type.*—Plant tissue culture.

*Time to produce a rooted liner.*—Summer: About 10 weeks at about 25 to 30° C. soil temperature. Winter: About 11 to 12 weeks at about 22 to 27° C. soil temperature.

Plant description:

*Growth habit.*—Self-heading, not vining, and self-supporting. Large size, mostly upright, slightly outwardly spreading; open. Appropriate for 15-cm and larger containers.

*Plant size.*—Height: About 76.5 cm. Diameter: About 112.6 cm.

*Plant vigor.*—Very vigorous.

*Crop time.*—About 7 months are needed to produce a finished plant in a 15-cm container from a single tissue culture-produced microcutting. About 12 months are needed to produce a finished plant in a 25-cm container from a single tissue culture-produced microcutting.

Foliage description:

*Petiole.*—Shape: Adaxial side slightly concave; abaxial side rounded. Size: About 40.6 cm long; about 13.9 mm in diameter immediately below leaf blade, about 26.6 mm in diameter immediately above base. Color: Newly unfolded leaf, adaxial: Lighter and slightly more brown than 187A near base; more brown than 187A in distal zone. Newly unfolded leaf, abaxial: Slightly more brown than 187A near base; similar to 187A in distal zone. A narrow ring of a color much darker than 187A at the juncture between petiole and leaf blade. Mature leaf, adaxial: Most similar to 200A with a slight undertone of a color darker than 187A. Mature leaf, abaxial: Between 200A, 200B and 187A near base; between 200A and 187A in distal zone. A narrow ring of a color much darker than 187A at the juncture between petiole and leaf blade.

*Petiole sheath.*—Shape: Rolled adaxially at all times, so that only abaxial side visible. Length: About 32.4 cm. Color: Proximal zone darker than 178A in the middle, approximately 185A near margins; distal zone varies between different combinations of 187A and 187B.

*Leaf blade.*—Aspect: Upper leaves relatively upright and slightly curving adaxially, so that abaxial surface exposed. Lower leaves approximately horizontal. Shape: Broadly ovate, asymmetric; apex acute; base between truncate and auriculate, asymmetric. Size: About 45.7 cm long, about 30.2 cm wide; length: width ratio about 1.5 to 1. Texture: Thick, leathery, glabrous, relatively glossy. Venation: Pinnate, prominent; midrib sunken in adaxial surface and protrudes from abaxial surface; primary veins are sunken in adaxial surface and protrude from abaxial surface. Color: Newly unrolled leaf, adaxial: Brown-maroon-green, incapable of precise color description, but darker and more brown than 147A. A line less than 1 mm wide along margin varies between 185A and 184A. Midrib similar to or slightly lighter than 199A near juncture with petiole; darker than 199A in distal zone. Portions of primary veins near midrib lighter and more green than surrounding tissue. Newly unrolled leaf, abaxial: Variable color between maroon, brown, purple and green. Many areas most similar to 165A with various degree of green undertones. A line less than 1 mm wide along margin varies between 185A and 184A. Midrib between 183A and 183B in proximal zone with short darker striae. (183A or darker); approximately 178A in distal zone. Primary veins usually more pale than midrib. Mature leaf, adaxial: Much darker than 147A. A line less than 1 mm wide along margin varies between 187A and 187B. Midrib between 146A and a color slightly darker than 147B near juncture with petiole; slightly darker in the distal zone (between 147A and 147B). Portions of primary veins near midrib similar to midrib. Mature leaf, abaxial: More brownish and slightly darker than 147A. A line less than 1 mm wide along margin varies between 187A and 187B. Midrib uneven color varying between different combinations of 200C, 200D, 166A or lighter, and 177A or lighter in proximal zone, with short darker striae (approximately 200B); most similar to 166A in distal zone. Primary veins usually more pale than midrib.

Inflorescence description:

*Flowering.*—Plants typically form inflorescences about 16 months after planting a tissue culture-produced microcutting.

*Inflorescence arrangement.*—Inflorescence erect, close to the shoot of origin, obscured by the surrounding foliage. One to 3 inflorescences in each floral sympodium.

*Fragrance.*—Not noticeable.

*Peduncle.*—Length: About 3.9 cm. Diameter: About 1.2 cm. Color:60A at base to 59A distally.

*Spathe.*—Shape: Boat-shaped, thick, fleshy; apex between acuminate and cuspidate; margin, entire. Length: about 14.3 cm. Width: about 7.7 cm. Length to width ratio: about 1.9 to 1. Depth: about 2.6 cm. Color: open front: 59A slightly darker at base; open rear: 59A, 59B with basal ⅓ slightly darker.

*Spadix.*—Shape: Cylindrical, tapering towards acute apex, with the strongest tapering at distal ⅓. Length: about 12.2 cm. Female, basal zone about 4.5 cm; the intermediate sterile zone and distal male zone combined, about 7.7 cm. Diameter: female zone, about 1.5 cm; sterile and male zones, about 1.1 cm. Color: female zone, 59A; sterile and male zones 69A to 68C.

*Pollen.*—Dehiscence about one to three days after spathe closes. Pink to cream colored in a liquid secretion.

*Seed production.*—Seed production not observed.

Roots description: Few thick main roots, orange-brown with dark red root caps. Numerous relatively thin lateral roots vary in color between cream and brown. Numerous thick aerial roots of different length and different shades of brown and purplish-brown colors. Many aerial roots have a short zone near tip of a red color (between 46A and 185A).

Disease and insect resistance: Plants of 'Rojo Congo', which are grown in commercial greenhouses and shadehouses, have not shown any unusual susceptibility to pathogens or insects common to Philodendron.

I claim:

1. A new and distinct cultivar of Philodendron plant named 'Rojo Congo' as described and illustrated herein.

* * * * *